US005602477A

United States Patent [19]
McCarthy et al.

[11] Patent Number: 5,602,477
[45] Date of Patent: Feb. 11, 1997

[54] NUCLEAR MAGNETIC RESONANCE FREEZING SENSOR

[75] Inventors: Michael J. McCarthy; David S. Reid, both of Davis, Calif.

[73] Assignee: The Regents of the University of California, Oakland, Calif.

[21] Appl. No.: 384,568

[22] Filed: Feb. 6, 1995

[51] Int. Cl.⁶ ..................................................... G01V 3/00
[52] U.S. Cl. ........................................... 324/315; 324/300
[58] Field of Search .................................... 324/300, 306, 324/308, 312, 315, 307, 309

[56] References Cited

U.S. PATENT DOCUMENTS

| | | | |
|---|---|---|---|
| 4,558,279 | 12/1985 | Ackerman et al. | 324/315 |
| 4,701,705 | 10/1987 | Rollwitz | 324/308 |
| 5,270,650 | 12/1993 | Schenz et al. | 324/300 |
| 5,371,464 | 12/1994 | Rapoport | 324/300 |

OTHER PUBLICATIONS

McCarthy et al., "Phase Volume Measurements Using Magnetic Resonance Imaging", Water Relationships in Foods, Edited by Levine and Slade, pp. 615–626, 1991.
McCarthy et al., "Magnetic Resonance Imaging Applications in Food Research", Trends in Food Science and Technology, Elsevier Science Publishers, pp. 134–139, 1990.
McCarthy et al., "Real Time Monitoring of the Extent of Freezing and Thawing in Foods", Symposium on Freezing Int. Un. Food Sci. & Tech., Toronto, 1991.

Primary Examiner—Louis M. Arana
Attorney, Agent, or Firm—John P. O'Banion

[57] ABSTRACT

A non-invasive apparatus and method for determining changes in the enthalpy of an object undergoing a freezing cycle using nuclear magnetic resonance (NMR) imaging (NMRI) techniques. Enthalpy is determined from the position of the ice interface of said object or, alternatively, from the liquid/solid ratio of the object.

10 Claims, 1 Drawing Sheet

FIG. - 1

FIG. - 2

NUCLEAR MAGNETIC RESONANCE FREEZING SENSOR

BACKGROUND OF THE INVENTION

The invention described herein was made in the course of, or under, a contract RP8012-11 with the Electric Power Research Institute.

1. Field of the Invention

This invention pertains generally to monitoring and controlling the freezing of foods, and more particularly to a non-invasive apparatus and method for using nuclear magnetic resonance imaging to determine the ice interface in the object which, together with the air temperature and air velocity, are used to measure enthalpy in food freezing operations. Alternatively, enthalpy can be measured from the ratio of liquid to solid portions of the object determined from nuclear magnetic resonance imaging or, for objects of substantially symmetrical geometric shape, from the liquid/solid ratio obtained by integrating the amplitude of nuclear magnetic resonance signals.

2. Description of the Background Art

Freezing is one of the major means of food preservation in industrialized countries of the world. The types of products which are frozen range from agricultural to animal food stuffs, and include fruits, vegetables, animal meats, fish, and dairy products. In addition to raw commodities, many formulated or "value-added" products are frozen. These include popular items such as pizza, TV dinners, ice cream, and fish sticks.

Preservation of food requires that it be maintained in a safe and nutritious state, and still taste good to the consumer. One of the primary goals of freezing is to limit the growth of microorganisms during prolonged storage. While freezing does not necessarily kill bacteria and mold, low temperatures associated with freezing limit metabolic processes necessary for them to duplicate. Excessive microbial loads may be reduced prior to freezing through blanching or other thermal treatments.

Temperature reduction during freezing also decreases the rate of chemical reactions that continue during storage. This impacts nutritional and sensory attributes, as many of the reactions may be degradative. For example, vitamins may break down, pleasing color attributes may change, or off-flavors may develop all due to chemical processes. Many frozen and thawed foods, however, are often indistinguishable from the fresh commodity. Overall, lowering the temperature of a food while converting water to ice helps limit the growth of microorganisms, slows deleterious chemical reactions and, in some cases, imparts desirable sensory qualities to the food.

Many types of freezers are available for food freezing. The type of freezer used varies with the product being frozen based on such factors as the final temperature to be reached, the size of the product, the thermal properties of the product, whether the pieces are to be frozen individually or as a group, and the amount of space available. Typically, freezers can be categorized as either batch or continuous types. In batch processes, the product is placed into the freezer and left to sit for a given time. In continuous processes, the product is conveyed through the length of the freezer on carts or conveyor belts. Combinations of batch and continuous modes are also possible.

A critical factor in all freezing operations is the "residence time" of the product; that is, the time in which the product remains in the freezer. For continuous freezers, this depends on the length of the freezer and the speed at which product is moved through the freezer. For batch freezers, this entails the amount of time the product is left in the freezer before removal. Residence time is a critical factor in food freezing, since a too short residence time will mean that the product has not reached its desired temperature. Conversely, a prolonged residence time means that product throughput could actually be increased.

The primary means of lowering temperature in freezers is through the compressor-based refrigeration cycle. Liquid refrigerant at low temperature and pressure is circulated through a heat exchanger (evaporator) in the freezer compartment. As heat is removed from the compartment, the refrigerant becomes a low temperature gas. A compressor converts this to a gas at high temperature and pressure. The gas condenses as it passes through a second heat exchanger (condenser) where the heat is exhausted to the surroundings. The cycle is completed as it passes through an expansion valve.

No hard data exist on the energy requirements for industrial freezing operations. However, an order of magnitude estimate can be made as follows. Assume a food product is cooled and frozen from 30° C. to –15° C. From ASHRAE tables, an average specific heat between 32° C. and 4° C. is about $C_p$=3.6 kJ/kg °C. A typical latent heat change between 0° and –15° C. would be 305 kJ/kg. Thus, the heat removed to cool and freeze 1 kg is $$25 \times 3.6 \text{ kj/kg °C.} + 15 \times 305 \text{ kJ/kg} = 395 \text{ kJ/kg}$$

or 147 kJ/lb. The true refrigeration load in a freezer is larger, as heat may be gained from the surroundings through insulation leaks and air changes, or through waste heat from lights, motors, or even people. As a conservative estimate, we assume these add 10% to the refrigeration load, or $$395 \text{ kJ/kg} + 0.10 \times 395 \text{ kJ/kg} = 435 \text{ kJ/kg}$$

For most industrial freezing operations, energy is expended in the compressor to compress refrigerant vapor. In essence, electrical energy is delivered to the compressor in order to continue the refrigeration cycle. The ratio of heat energy absorbed in the evaporators to the energy input to the compressor is given by the coefficent of performance (COP):

$$COP = \frac{\text{Refrigeration Capacity}}{\text{Compressor Power}}$$

Typical COPs for industrial refrigerants range from 4.59 for R-22 to 4.77 for ammonia, given an evaporating temperature of –15° C. and a condensing temperature of 30° C. These values account for the inefficiency of compression, such as, losses in the compressor clearance volume. Using an average of 4.65, the minimal electric energy input for the situation described above is:

$$435 \text{ kJ/kg} \div 4.65 = 94 \text{ kJ/kg}$$

Next, if one assumes the compressor motor is 80% efficient, the electrical consumption becomes $$94 \text{ kJ/kg} \div 0.80 = 117 \text{ kJ/kg}$$

Typically, there is about a 30% additional energy cost from such things as circulating air through blast freezers or moving product on conveyors. This increases electrical consumption to $$117 \text{ kJ/kg} + 0.30 \times 117 \text{ kJ/kg} = 152 \text{ kJ/kg}$$

or 57 kJ/lb of frozen food. In 1990, about 28 billion pounds of food were frozen. Thus, we might estimate the electrical consumption for food freezing to be on the order of $$57 \text{ kJ/lb} \times 28 \times 10^9 = 1.6 \times 10^{12} \text{ kJ}$$

or about $4.5 \times 10^8$ kW·hr per year.

The goal in freezing is to remove enough heat from the product to bring it to its desired enthalpy value. The enthalpy of the product upon removal from the freezer should be the same as the value it has during frozen storage. If residence time is too short and exit enthalpy is too high, further heat will be removed during storage. This is undesirable as facilities designed for frozen storage are not as efficient at removing heat as freezers. If freezer residence time is too long, excess electrical power will be consumed without further reduction in product enthalpy. As an example, if a product is sufficiently frozen in 15 minutes but remains in a freezer for 18 minutes, the operation consumes 20% more energy than necessary. If energy conservation of just 1% could be realized, this could mean savings on the order of 4.5 million kW·hr per year.

Freezing rates or freezing times can be defined in a variety of ways, including:

(a) the change in temperature with time at some point (dT/dt);

(b) the velocity at which the ice interface advances (dx/dt);

(c) the total time required to traverse a given temperature interval ($t_f$);

(d) the rate of enthalpy change (dH/dt) or time required for a given enthalpy change.

Traditionally, the primary means of measuring or predicting food freezing rates have been through thermometric measuring during freezing, or mathematical modelling. In the former, the time required for a given temperature change to occur is assessed by placing thermocouples within a sample during freezing. This provides a recorded history of temperature profiles within the sample. Freezing rate has been defined in several ways, such as by dividing the surface to center distance by the time required to reach 0° C. and the thermal center to reach 5° C. below the freezing temperature. More common, however, is the concept of "freezing time" such as the time required for the slowest cooling point to decrease from 0° C. to −5° C. Use of thermocouples, however, is undesirable since they may provide additional heat conduction paths to the same or alter air flow patterns. Additionally, such an approach does not measure the variable of most interest, namely the change in enthalpy with time.

With regard to mathematical modelling, Planck's equation, the simplest of available freezing models, describes this time $t_f$ as:

$$t_f = \frac{\rho \Delta H_L}{T_f - T_\infty} \left[ \frac{Pa}{h} + \frac{Ra^2}{k} \right]$$

where r is the density of unfrozen material, $\Delta H_L$ is the latent heat of water in the product, $T_f$ is the freezing temperature, $T_\infty$ is the final temperature, h is the surface heat transfer coefficient, k is the thermal conductivity of ice, a is a characteristic dimension, and P and R are shape factors. Planck's model is only a rough approximation to the freezing time, as it assumes all the latent heat is removed at one temperature, and that thermal conductivity is constant throughout the process. While Planck's model is a useful equation because it qualitatively describes the factors important to freezing rates, it is untenable to obtain an exact solution for heat conduction in a system undergoing a gradual phase change, and in which the pertinent physical properties vary with temperature.

However, when considering energy costs, defining freezing rates and freezing times in terms of enthalpy changes is more useful. At constant pressure, the enthalpy difference $\Delta H$ is just the heat gained or lost in the process. For example, if a product is cooled and frozen from an initial temperature $T_R$ to a steady-state at temperature $T_\infty$, the enthalpy difference is the amount of heat removed by the freezer to bring the product to its steady-state. The time required for this to happen is subject to the tolerance specified for reaching the final state. Cooling and freezing represent a transient process approaching a steady-state. In practice, one could define the freezing time as that required for some percentage, say 95%, of the total change to be made.

Significantly, there are no in-line sensors available for assessing freezing rates or when freezing is complete. Measurements using conventional temperature probes within the product are necessarily invasive and are difficult to monitor on a routine basis. Conventional calorimeters, on the other hand, typically make steady-state measurements of products inside the calorimeter itself. As such, they give no information on the required freezing time. Therefore, there is a need for a method and apparatus for in-line, non-invasive assessment of the freezing process. The present invention satisfies this need, as well as others, and overcomes the deficiencies in prior devices.

SUMMARY OF THE INVENTION

By way of example, and not of limitation, the present invention generally comprises a non-invasive apparatus and method for determining changes in the enthalpy of an object undergoing a freezing cycle from the location of the ice interface using nuclear magnetic resonance (NMR) imaging (NMRI) techniques, combined with the air velocity and air temperature measurements. The NMR image data, air velocity data, and air temperature data are calibrated by utilizing a calorimeter to enable enthalpy measurements during the transient and steady-state parts of freezing. As result, the position of the ice interface can be correlated to the enthalpy of the object. Further, images of the total liquid portion and the total solid portion of the object can be acquired or, alternatively, for objects of substantially symmetrical geometric shape NMR signal amplitudes can be integrated to determine liquid and solid portions of the object, and the enthalpy determined through a correlation of the ratio of frozen/unfrozen portions of the product with the calorimetric enthalpy unique to the freezing conditions. The enthalpy of the object is then used to control the food freezing operation.

The present invention provides for measurement of enthalpy during the transient and steady-state parts of freezing. Advance of the ice interface has until now been impossible to visualize except in clear solutions. The present invention, however, employs nuclear magnetic resonance imaging techniques to follow the formation of ice. By correlating NMR imaging with calorimetry, the present invention providers an in-line, non-invasive sensor for monitoring energy flow during food freezing.

The apparatus of the present invention generally comprises an RF probe encircling a conveyor, tube or the like which is carrying the product to be frozen, a plurality of magnets for generating a magnetic field around the conveyor, magnetic field gradient coils positioned between the magnets and the RF probe, a power supply for the gradient coils, a transmitter and receiver coupled to the RF probe, and a central processing unit coupled to the transmitter and receiver and gradient coil power supply. In operation, an image of the liquid protons from the water phase is acquired using a standard NMR imaging pulse sequence to measure the spatial distribution of spins, which is repeated N−1 times (where N is usually a power of 2). The interface location is then measured using standard edge detection techniques. The location of the interface, air velocity, and air temperature are used in conjunction with a calibration based on differential calorimetry measurements to determine enthalpy. For objects of substantially symmetrical geometric shape, imaging is unnecessary and the integrated amplitude of NMR signals can be used to determine the liquid and solid portions of the object. The ratio of liquid to solid portions of the object, air velocity, and air temperature are used in conjunction with a calibration based on differential calorimetry measurements to determine enthalpy. The change in enthalpy is then compared to that required for successful operation of the freezing system.

An object of the invention is to make non-invasive enthalpy measurements.

Another object of the invention is to provide for non-invasive in-line measurement of the extent of freezing a food product.

Another object of the invention is to provide for non-invasive at-line measurement of the extent of freezing a food product.

Another object of the invention is to provide for non-invasive on-line measurement of the extent of freezing a food product.

Another object of the invention is to reduce energy consumption during food freezing.

Another object of the invention is to measure the enthalpy of a product in a non-invasive manner without reference to a particular model of the product behavior.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
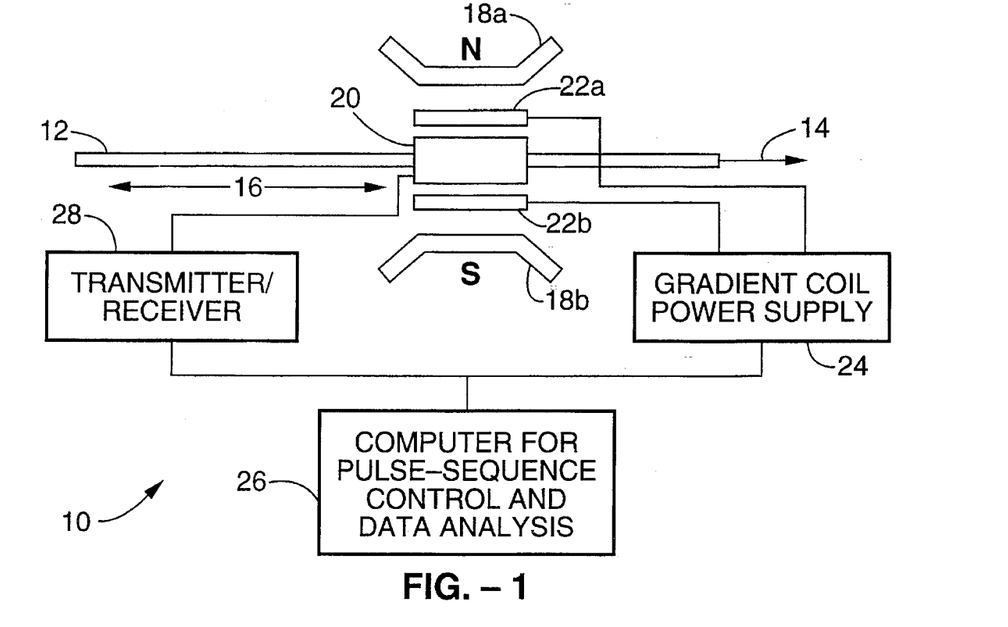
FIG. 1 is schematic diagram of a nuclear magnetic resonance freezing sensor in accordance with the present invention.

FIG. 1 schematically depicts a nuclear magnetic resonance freezing sensor 10 in accordance with the present invention. Magnetic resonance results from the interaction between atomic particles, electrons and the nuclei, and an external magnetic field. This interaction is similar to that observed when iron filings are placed near a bar magnet. The filings become oriented and a magnetic field is induced in the metal. However, unlike the physical motion of the filings, the physical orientation of the atomic particles is not altered. Only the magnetic moment of the atomic particles is influenced (at most common magnetic field strengths). Resonance is observed in these systems because they absorb and emit energy at specific frequencies. The specific frequency depends on the individual atomic particle and the strength of the applied magnetic field. When the atomic particle is a nucleus the phenomenon is termed Nuclear Magnetic Resonance (NMR). Not all nuclei exhibit magnetic resonance, however. A nuclei has a magnetic moment only if the spin angular moment is non-zero.

Nuclear magnetic resonance imaging (NMRI) is an NMR technique which provides spatial localization of the NMR signals from a sample. Signals from many neighboring spatial locations are used to generate an image of nuclei density or some other property. NMRI is based on degrading the homogeneity of the external magnetic field in a specific way, resulting in a known frequency variation across the sample. This variation is usually achieved by applying a linear magnetic field gradient. If the effects of the shielding constant are ignored, the frequency of excitation and detection for an NMR experiment, $\upsilon$, is given by the Larmor equation, $\upsilon = \gamma B_o/2\pi$, where $\gamma$ is the gyromagnetic ratio and $B_o$ is the magnetic field strength. By applying a linear field gradient in the z direction, the frequency becomes a function of position: $\upsilon(z) = \gamma(B_o + g_z z) 2\pi$ where $g_z$ is the strength of the magnetic field gradient in the z direction. Using three orthogonal gradients during an NMR pulse sequence a two or three dimensional NMR image can be acquired. The principal advantage of NMRI is that the sample is unaffected by the measurement (at common magnetic field strengths) and opaque systems can be studied.

It is possible to use NMRI to measure changes in enthalpy in moving and stationary systems using pulse sequences capable of spatially encoding the NMR signal wherein the products are subjected to a constant magnetic field of strength $B_o$ and a magnetic field gradient, g. After the spin systems have aligned with the imposed magnetic fields, they are disturbed by a radio frequency pulse that "tags" a region of the movement. Phase encode imaging produces direct images for stationary, uni-directional and more complex movement. In the case of one-dimensional, steady movement, this technique can be described as follows. Letting z(t) be the position of a spin at time t, then, $z(t) = Z_0 + w t$ where $Z_0$ is the position of the spin at time zero and w is the velocity of the spin. We call $g_z$ the applied magnetic field gradient in the flow direction, then, use Bloch equations to show that the phase of the magnetization is given by $$\phi = \gamma \int_0^t z(s) g_z(s) ds = \gamma(Z_0 m_0 + w m_1)$$

where $m_0$ and $m_1$ are the zeroth and first moments of the gradient, respectively, namely, $$m_0 = \int_0^t g_z(s) ds, \quad m_1 = \int_0^t s g_z(s) ds$$

The applied gradient is designed such that $m_o \neq 0$ but $m_1 = 0$. Under these conditions, the phase angle is proportional to the position of the spin and is not influenced by the velocity of the spin. Just as the phase of the magnetization can be used to measure the spin density distribution in standard NMRI, a properly designed gradient allows the spin density distribution in a moving object to be measured in a sample.

As can be seen from FIG. 1, the NMR freezing sensor 10 in accordance with the present invention is situated adjacent to a conveyor 12 on which a food product 14 moves and which should have a sufficient entrance length 16 from any product source to hold the products to be evaluated. Permanent magnets 18a, 18b are radially positioned on each side of conveyor 12 to establish a magnetic field through the product 14, one magnet having its north pole facing the conveyor 12 and the other magnet having is south pole facing the conveyor 12. Conveyor 12 extends through an RF probe 20, and gradient field coils 22a, 22b are positioned between magnets 18a, 18b and RF probe 22, respectively. In order to minimize the generation of unwanted eddy currents in magnets 18a, 18b, gradient field coils 22a, 22b (and hence RF probe 20) should be physically separated from magnets 18a, 18b by a distance sufficient to prevent coupling or the gradient field coils should be shielded. Preferably, the gradient rise/fall times should be sufficiently fast so as to allow for gradient waveforms which compensate for velocity and acceleration ($m_1=0$ and $m_2=0$). Also included is a power supply 24 for powering gradient field coils 22a, 22b. A control processor 26, which can be a central processing unit, microcomputer or the like, is used to generate the pulse sequences, to control the acquisition of images, to evaluate the acquired images, and to determine the ice interface and enthalpy of the product. Control processor 26 is coupled to a transmitter/receiver 28 and power supply 24. Power supply 24 is coupled to gradient field coils 22a, 22b and transmitter/receiver 28 is coupled to RF probe 20. Magnets 18a, 18b, RF probe 20, gradient field coils 22a, 22b, power supply 24, and transmitter/receiver 28 can be of a type used in conventional nuclear magnetic resonance imaging or spectroscopy equipment.

Figure 2:
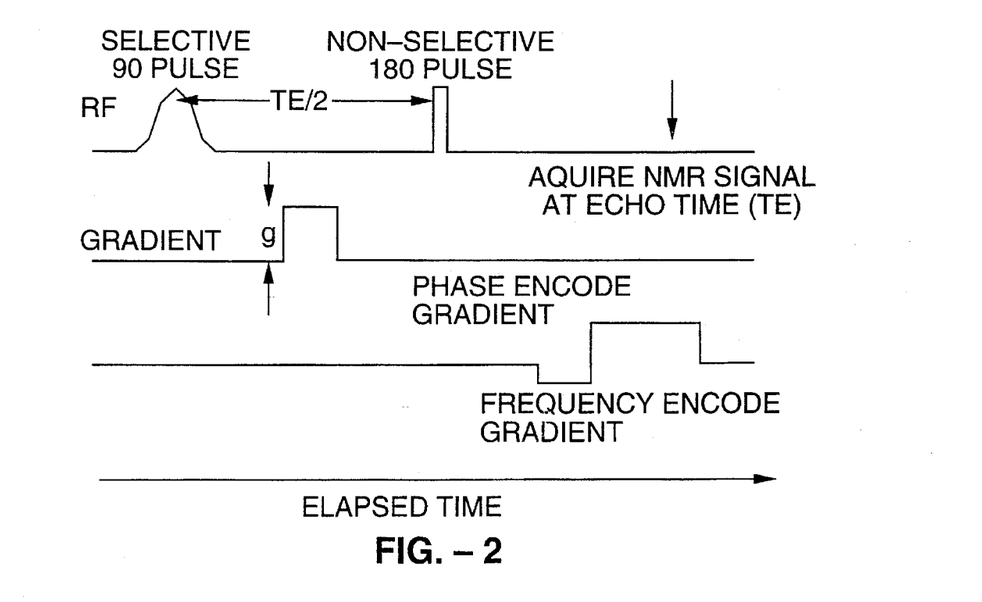
FIG. 2 is a timing diagram showing an NMR pulse sequence used in conjunction with the apparatus shown in FIG. 1.

Referring to FIG. 2, an exemplary sequence of the RF and gradient pulses used to generate the NMR images is shown. This sequence can be tailored so as to provide optimal data for any product flow rate by setting the gradients such that the NMR signal recorded encodes only intensity and position, and the maximum position measured is just slightly larger than the product of interest. The field of view in each direction would be set to be just greater than the maximum length of the product in that direction. The frequency encode direction would have the minimum field of view necessary to prevent aliasing of the image. The sequence is repeated N−1 times (where N is usually a power of 2). Gradient pulse g would change in magnitude for each repetition from −g to g. The maximum value of g is set by the field of view in the phase encode direction. Gradients for the selective pulse and frequency encoding may be velocity compensated if necessary to reduce artifacts in the final image. Gradient pulses for the pulse sequence in FIG. 2 are drawn without velocity compensation.

EXAMPLE 1

Overall Strategy

A variety of foods were placed within the confines of an NMR imaging coil and allowed to freeze. As freezing progressed, NMR images were collected at regular intervals in order to monitor spatial location of frozen and unfrozen water, air velocity and air temperature were recorded. In some experiments, thermocouples were placed along the central axis of the product to simultaneously map the time course of internal temperature profiles. In other experiments, samples were periodically removed from the freezer and placed immediately in a differential calorimeter. This allowed us to follow the amount of heat removed at any time during the freezing process.

EXAMPLE 2

Sample Preparation

The types of foods studied are listed in Table 1.

TABLE 1

Foods Studied by Nuclear Magnetic Resonance Imaging

| Sample | Type of Freezer | Geometry/mode | Comments |
|---|---|---|---|
| Carrot | Cryogenic | Cylinder/3-D | |
| Cantelope | Cryogenic | Cylinder/3-D | |
| Potato | Cryogenic | Cylinder/3-D | |
| Yellow Squash | Cryogenic | Cylinder/3-D | |
| Onion | Cryogenic | Cylinder/3-D | |
| Beef Hot Dogs | Cryogenic | Cylinder/3-D | As is |
| Orange Juice | Cryogenic | Cylinder/3-D | In plastic tubes |
| Vanilla Ice Cream | Cryogenic | Cylinder/3-D | In plastic tubes |
| Carrot | Air blast | Cylinder/3-D | Ends chopped |
| Potato | Air blast | Cylinder/3-D | |
| Broccoli | Air blast | Irregular/3-D | Ends |
| Corn Cobs | Air blast | Irregular/3-D | As is |
| Chicken Legs | Air blast | Irregular/3-D | As is |
| Peas | Air blast | Cylinder/3-D | In plastic tubes |
| Beef Round-steak | Air blast | Slabs/1-D | |
| Beef Round-steak | Air blast | Slabs/3-D | |
| Ground Beef | Air Blast | Slabs/1-D | |
| Potato | Air blast | Irregular/3-D | As is with skin |

All samples were purchased at a local supermarket. Most products were obtained at room temperature or at refrigerator temperatures. In a few instances, the frozen product was used and allowed to thaw prior to examination.

In some cases, the samples were imaged in their existing shapes. In other cases, the samples were cut into cubes (3×3×5 cm) or cylinders (3.5 cm diam×6 cm). This facilitated mathematical modelling of the freezing process.

All samples were weighed on a top loading electronic balance (PE 2000, Mettler Corp., Highstown, N.J.) prior to introduction to the freezer. This allowed us to normalize heat change and NMRI signal intensity data. Both three-dimensional and one-dimensional heat flow was studied. In the former case, samples were placed directly on a push rod and centered within the 10 cm tube through which cold air was circulated, so that air was allowed to reach the product on all sides. In the latter case, the sides perpendicular to the air flow were covered with ½" foam insulation; here, heat removal was primarily from the front and rear faces of the sample.

EXAMPLE 3

Freezer Conditions

Two air blast freezers and one cryogenic freezer were used in these experiments. The air blast freezers were modified so that they could deliver cold air through an insulated 6 m section of PVC pipe (10.2 cm ID). The PVC pipe continued through the center of the NMRI bore, before returning to the intake of the freezer. The two mechanical freezers were a Frigoscandia (Sweden) laboratory air-blast freezer and a Conrad (Rockford, Ill) air-blast freezer. These gave air flows of 0–10 m/s at temperatures between −15° C. and −35° C. Air flow rate was controlled with a baffle which could be slid into the interior compartment of the freezer. Temperature was adjustable by means of a thermostat on the freezer.

Cryogenic freezing was accomplished with a Union Carbide cryogenic unit. Liquid nitrogen (250 L at 20 PSI) was delivered through a spray nozzle centered within the tube, and about 2 m away from the sample.

The sample was introduced in the freezer by means of a push rod. The rod was equipped with a platform made of two 0.64 cm diameter wood dowels. These contacted the sample at two points and kept it suspended above the tube, and centered within the diameter of the tube. The rod was 1.2 m long and inserted after removing an endcap from where the PVC tube exits the magnet. A locating pin at the end opposite the sample fixes the sample so that it is directly within the confines of the imaging coil.

EXAMPLE 4

Differential Calorimetry

A differential compensated type calorimeter was used to monitor heat removal during freezing. Two identical vessels were used so that any heat loss from the sample chamber was compensated for by the reference chamber. The sample vessel was controlled to eliminate any temperature differential that developed between the two vessels once the sample was introduced. The amount of energy introduced into the sample vessel measured the heat effect. Careful control of the calorimeter temperature was not required, as the calorimeter fluid was at the same temperature as that of the surrounding room.

The vessels were made from silvered Dewar flasks 27.5 cm in diameter and 28 cm high. The inner chambers were stainless steel cups 15 cm in diameter and 15 cm deep. The covers were made from 8 mm thick PVC end cap (30.5 cm ID); this could be readily machined and tapped to provide needed features such as doors and screw supports. Each cover was insulated with 5–6 cm of spray foam (Insta-Foam Products, Joliet, Ill.) such that it fit snugly over the Dewar.

The sample chamber contained a heater constructed from 3.6 m of 0.25 mm diameter Teflon-coated constantan wire (Omega, Stamford, Conn.) wrapped around a 1.27 cm diameter plexiglass rod. The heater resistance was 36 ohms at room temperature. A mixer motor (Talboy Model 104, Emerson, N.J.) was mounted to the top of the cover, with a 9.5 mm diameter stainless steel shaft leading into the chamber and terminating in a 3-paddle mixer. A 7.5×10 cm trap door on the cover allowed samples to be introduced. To keep buoyant samples submerged in the water, a 3-sided plastic basket was fitted to a 6.3 mm plastic rod running through the chamber. The basket could be swivelled or raised and lowered in the chamber to trap the sample below the water.

Each of the vessels was filled with water at the same (room) temperature; the differential temperature was monitored with an 8-junction copper-constantan thermopile with alternate junctions in the sample and reference chambers. The output of the thermopile was amplified by an OMNI IIA DC millivolt amplifier (Omega, Stamford, Conn.) and directed to a BD 40 linear chart recorder (Zipp and Konen, Holland). The amplifier gain and recorder sensitivity were set to give a full scale reading corresponding to 1° C. temperature differential.

The heater was powered by a 50 V power supply (VIZ Mfg., Philadelphia, Pa.). Voltage and current remained constant over the course of an experiment and were monitored by a built-in voltmeter and ammeter. A cross-check of power input was made by reading the voltage directly across the 36 ohm heater wire. The heater was turned on and off by a DPDT switch that activated a XL-10 cumulative timer (Kessler-Ellis, Atlantic Highlands, N.J.) whenever the heater was on. Care was taken such that heater leads and switches had minimal resistance (<0.1 ohms).

Samples were removed from the freezer at regular intervals during transient freezing; a new sample was placed in the freezer for each time interval to be explored. By compiling data for several samples, a plot of heat removal versus time in the freezer could be formed for each set of freezer conditions. Once removed from the freezer, the samples were immediately introduced into the sample vessel. As heat was dissipated into the sample chamber, a temperature difference developed between sample and reference chambers. The controlled heater was used to eliminate any temperature differential. The amount of energy introduced into the sample by the heater measures the amount of heat removed from the sample within the freezer.

EXAMPLE 5

Temperature Profiles

Temperatures within a sample were monitored by a series of thermocouples placed along the sample axis parallel to the air flow. Four thermocouples were constructed from 0.010" diameter copper and constantan wire. A trial and error procedure was required to find the proper length of wire that caused the least noise in the NMR images. The thermocouples were inserted at approximately 7 mm intervals between the front surface and center of the sample. The leads were fed out through a 2 mm opening in the PVC pipe and directed to a Molytech 32-channel datalogger (Pittsburgh, Pa.). The datalogger was set to make recordings at times while images were not being taken. By staggering collection of temperature and NMR image data, the best image quality was maintained in the NMR images.

EXAMPLE 6

NMR Imaging

The sample was placed in the freezer tube and within a 10 cm homemade "birdcage" imaging coil. The coil size was selected so as to maximize the filling factor of the RF coils, thereby enhancing the signal-to-noise ratio of the data. NMR images were obtained using a General Electric CSI-2 Fourier Transform NMR Spectrometer, tuned to the hydrogen nuclear resonance frequency of 85.53 MHz and another General Electric CS1-2 Fourier Transform NMR Spectrometer tuned to a hydrogen nuclear resonance frequency of 25.9 MHz. The 30 cm horizontal bore of the 0.6-Tesla superconducting magnet permits imaging of objects having diameters up to 14.6 cm.

A spin-echo pulse sequence (General Electric Medical Systems, Fremont, Calif.) was used in imaging the samples. Adjustment of echo delay (TE, the period during which sample magnetization dephases, then rephases) and interpulse delay allowed T1 and/or T2 relaxation-weighted image contrast (8), thereby enhancing structural differences.

Echo delays were 15 ms; interpulse delays varied from 200 to 400 ms.

Images were plotted directly to a Tektronix 4634 plotter (Beaverton, Ore.). Raw data files were also kept and in most cases ported to a Apple MacIntosh II computer (Cupertino, Cailf.). This allowed further analysis of the data. For example, images were color-enhanced through the Spyglass software program (Spyglass, Inc., Champaign, Ill.); this produced images in which signal intensity bands were transformed to a gradation of colors. In other cases, data was analyzed with the MathCAD mathematics program (Math-Soft, Inc., Cambridge, Mass.). This allowed for statistical analysis of the signal intensity variation near the freezing interface.

EXAMPLE 7

Enthalpy Based Freezing Models

Data on interface position, heat removal, air temperature, air velocity and temperature profiles were compiled and analyzed in terms of an enthalpy-based freezing model which is available for PC and MacIntosh computers. This is a finite element model which solves the differential equation for enthalpy change involving a phase change:

$$\frac{\partial H}{\partial t} = \frac{1}{r^m} \frac{\partial}{\partial r} \left[ r^m k \frac{\partial T}{\partial r} \right]$$

where H is the enthalpy, t is time, T is temperature, and r is radial distance. The symbol m=0, 1, or 2 for rectangular, cylindrical, or spherical coordinates, respectively. The problem is approached by solving heat balance equations for each of the n nodes of a finite element grid. For the ith node at the jth unit of time, the enthalpy accumulated in the element is given by the difference between the heat flowing in and out of the element. Thus, $$V_i \left[ \frac{H_i^{j+1} - H_i^j}{\Delta t} \right] = A_{i+\frac{1}{2}} k_{i+\frac{1}{2}} \frac{[T_{i+1}^j - T_i^j]}{\Delta r} - A_{i-\frac{1}{2}} k_{i-\frac{1}{2}} \frac{[T_i^j - T_{i-1}^j]}{\Delta r}$$

Where A is the cross-sectional area and V the volume of the element. At the surface (i=n), the conductive heat transfer term (kAΔT) is replaced by the convective heat transfer term (hAΔT). To solve this system of equations, the thermal properties of the material must be known as a function of temperature. These include the thermal conductivity k, the heat capacity $C_p$, and the density r. These can be obtained from tables or estimated from the fat, water, and solids composition of the product. In addition to the material properties, the surface heat transfer coefficient h is required.

EXAMPLE 8

Results

A. NMR Images During Freezing

Images were plotted on a 250×350 pixel screen. A 10 cm×8 cm area was scanned by the NMRI, giving an image resolution of 340 mm/pixel. In some cases, internal structure of the food was highlighted. This was particularly true of samples such as carrots, onion, corn, and chicken pieces.

Bright areas in each image indicated regions of high signal intensity and therefore of high water mobility. Thus, these areas show where water exists in the liquid state. As time progresses, part of these regions become dark (low signal intensity) and show where ice has formed. The region of the ice-water interface appears as a line where the intensity shifts abruptly. In other words, loss of signal intensity occurs upon freezing. On closer examination, the transition from high intensity to low intensity occurs primarily over a 1 mm distance. The interface is defined as being the position in the image where the variation in intensity is highest.

As freezing progresses, the intensity of the outer regions of the food tended to become similar to the background value. In addition, the transition from high to low signal regions became more gradual, most likely due to the three-dimensional nature of the freezing process; that is, freezing occurs both radially and longitudinally. For the cylindrical samples, as freezing continued the initially cylindrical volume of unfrozen water became smaller in all directions and more like a spherical ellipsoid. Thus, signal averaging across the radial direction produces a steeper slope and a lessening of overall intensity.

Ice formation could be visualized in most of the foods imaged. One exception was beef hot dogs. Here, a relatively high intensity signal remained within the confines of the object even though calorimetry data showed that freezing was complete. This may be due to the relatively high fat content of the food (28%). In these particular experiments, full discrimination was not available between mobile protons associated with fats versus those of water. Future research may aim at resolving images based on their water or fat content. In practice, high fat meats are not a major part of the industrially frozen food market. Indeed, hot dogs are traditionally offered to the consumer refrigerated but unfrozen; consumers may then choose to freeze them. We were able to see ice development in other meats which are more often frozen, such as fish, chicken, or ground beef. We also were able to see ice development in high fat frozen dairy foods, such as ice cream.

With chicken legs, there were also indications of the contribution of fat to the NMR signal. In the images, signal intensity remained in the region of the bone and skin after freezing was complete. For the bone, this may be due to the relatively high lipid content in the bone marrow. Near the skin, there was an obvious subcutaneous layer of fat below the skin and above the muscle. Unlike the case with hot dogs, where fat is homogeneously distributed, the fat is structurally confined in the chicken. Thus, we could follow ice movement in the chicken leg and correlate it with the progress of freezing as studied by calorimetry.

For most foods examined, ice initially formed at the perimeter and moved towards the center of the product. In some cases, one-dimensional heat flow was examined by insulating the sides of the food parallel to the air flow. Here, the ice advanced as two interfacial fronts beginning at the front and rear surfaces of the product. The front interface moved at a rate faster than that developing from the rear side; the final loss in signal intensity occurred at a position behind the center of the product. This observation suggests that the rate of heat removal is not uniform over the whole product. In particular, the rate of heat transfer is greater at surfaces directly exposed to air flow. This reinforces the theory that the heat transfer coefficient (h), common to most heat transfer descriptions, is actually a value averaged over the entire surface of the product.

In other cases, three-dimensional heat flow was examined. Here, the ice advanced from all surfaces of the product towards the interior. Again, freezing is not symmetrical as the ice interface tends to converge at a point behind the center and closer to the rear of the product.

In one instance, the ice did not develop as a uniform front. This was seen in corn cobs. Here, the signal intensity associated with different kernels disappeared at different times. In the images obtained, kernels near the front and bottom were more likely to freeze first. However, some kernels may remain unfrozen even though its surrounding neighbors are frozen. One hypothesis as to what is happening is that some kernels are undercooled for a longer period of time before crystallization begins.

Two additional factors are noteworthy when assessing signal intensity and interface position. The first relates to the temperature dependency of the NMR signal. At lower temperatures, proton mobility is decreased as randomization of an initially polarized population of protons is diminished. This results in greater initial net magnetization. The signal intensity ($S_w$) is inversely related to the absolute temperature by:

$$S_w = \rho_{wl} \left( \frac{1}{\theta} \right) \exp\left( -\frac{TE}{T_{21}} \right)$$

where $\rho_{wl}$ is the density of liquid water nuclei, TE is the echo time, $T_{21}$ is the spin-spin relaxation time, and $\theta$ is the absolute temperature.

Second, temperature also affects $\rho_{wl}$ at temperatures below the initial freezing temperature ($T_m$). As temperature is lowered below $T_m=-1.2°$ C., the fraction of unfrozen water decreases as the liquid phase becomes increasingly concentrated in solutes. For example, for equilibrated potato at a temperature just above $-1.2°$ C., the 80% water content exists in the liquid state. At T=$-5°$ C., the percent of unfrozen water is 39%, the remaining 41% exists as ice. As the system is progressively cooled, a temperature is reached below which no further freeze-concentration occurs. At lower temperatures, the liquid phase becomes glassy. The temperature at which the system enters the glass phase is denoted $T_g'$. This means that while temperature gradients exist across the object, frozen regions more centrally located will contain more unfrozen water than those near the exterior. In relation to imaging capability, each volume element (voxel) containing liquid water may not contain the same amount of liquid water as surrounding voxels.

It was found that, at a given time, NMR signal intensity would vary in a region over which ice was still actively developing. Comparison of signal plots with and without $1/\theta$ temperature correction, however, show that while the absolute value and temperature sensitivity would be expected to differ, the transitions between different regions still occurred at the same temperatures. At positions where $T>T_m$, maximum liquid water exists and the signal is greatest. At temperatures $T<T_g'$, maximum ice formation has occurred and the signal takes its lowest value.

B. Heat Removal During Freezing

1. Enthalpy Measurements

The sample and reference chambers were initially at the sample temperature and showed no change in differential temperature. The mixer was then turned on and, due to frictional heating, contributed to an increase in temperature at a rate of 0.018° C./min. A frozen sample of beef kept at $-32°$ C. was introduced, causing the temperature to drop. After about 1 minute, the heater was switched on and the temperature rose. Heating of the chamber was done in several steps to allow time for heat transfer into the sample. The measurement was finished when the temperature reached the extrapolated calorimeter temperature.

The enthalpy change per gram of frozen product, between room temperature ($H_{RT}$) and the frozen storage temperature ($H_T$) is given by:

$$\Delta H = H_{RT} - H_T = \frac{V \cdot I \cdot t}{w}$$

where V is the heater voltage, I is the current, w is the sample weight, and t is the total time the heater was on.

2. Calorimeter Control Experiments

The first test of the calorimeter was to make sure that no significant differential heat losses occurred between the vessels. This was examined by placing cold or hot water in each of the chambers and monitoring the temperature difference. That difference ($\Delta T$) between chambers remained constant for at least 30 minutes. In practice, real heat losses should be less because near adiabatic conditions were maintained by keeping the calorimeter fluid near the surrounding room temperature.

A second test of the system was to ensure that the temperature increase due to the mixer was predictable. A food sample was placed in the water in the sample chamber and both were allowed to equilibrate to room temperature. $\Delta T$ was followed after turning on the mixer. The temperature rise was linear over the temperature range used.

The calorimeter was further checked and calibrated by measuring enthalpy changes for known weights of pure frozen water. For a sample frozen to some temperature T<0° C., the enthalpy change is given by $$\Delta H = C_{p,ice} w(0-T) + w\Delta H_{lat} + C_{p,H2O} w(T_c - 0)$$

where $T_c$ is the calorimeter temperature, $C_{p,ice}$=1.99 J/g °C., $C_{p,H2O}$=4.19 J/g °C., $\Delta H_{lat}$=333.6 J/g, and w is the sample weight. A plot of the measured versus calculated enthalpy for several weights of water showed the linear regression line through this data to have a slope of 0.997 (r=0.99), suggesting that there was less than 0.3% heat loss from the calorimeter. In practice, the measured enthalpy for other samples could be corrected by multiplying by a factor of 0.997.

Another check was to measure the enthalpy versus temperature for several food products at steady state. Although our main calorimetry measurements were for transient freezing, no literature values exist for comparison. Steady-state measurements on beef, egg white, applesauce, and white bread were made as literature data were readily available for these products. For comparison, enthalpy changes were converted to a reference of H=0 J/g at $-40°$ C. The data were reproducible for triplicate measurements, with a range of ±4 to ±11 J/g. As expected, the enthalpy increased at higher temperatures and showed the most change at temperatures approaching the freezing point. The results were similar, particularly for beef and applesauce. The lack of perfect agreement was not surprising, as there were likely to be compositional differences between the samples used in this and other experiments.

3. Calorimetric Measurements of Unfrozen Water

One question of importance in food freezing is how much water remains unfrozen after steady-state freezing has been reached. The amount of unfrozen water can be determined both by calorimetry and NMR techniques. In these initial experiments, we wished to evaluate the use of the described differential compensated calorimeter for this purpose.

A phase diagram was derived from enthalpy measurements on 20% sucrose. This diagram shows the concentration of sucrose remaining in the unfrozen liquid phase as a function of the equilibrium freezing temperature. This curve was developed by first calculating the amount of ice formed at each temperature. If $T_f$ is the freezing temperature, the weight fraction of ice formed (y) can be calculated from:

$$\Delta H = (1-x)C_{p,H2O}(T_c - T_f) + y\Delta H_{lat} + yC_{p,ice}(T_f - T) + (1-y-x)C_{p,H2O}(T_f - T) + xC_{p,solids}(T_c - T)$$

where x is the weight fraction of solids, 1−x the fraction of water, 1−y−x the fraction of unfrozen liquid at temperature T, and $C_{p,solids}$ is taken as 1.256 J/g °C. Given the amount of ice frozen at a specific temperature, the concentration of solute in the unfrozen liquid is x/(1−y−x). This equation was used to determine the solute concentration in the unfrozen liquid at each frozen storage temperature. A phase diagram was also derived from freezing point measurements of sucrose solutions of varying concentration. Agreement between phase diagrams derived in different ways shows that the calorimeter can accurately measure the amount of ice formed at various freezing temperatures.

4. Enthalpy Changes During Transient Freezing

Enthalpy is shown as the amount of heat removed by the freezer from a sample that was initially 25° C. Here, the term enthalpy is used in a restricted way and does not imply that the sample was at thermal equilibrium. Indeed, there was a progression of the ice interface during freezing, while thermocouple measurements show a thermal gradient exists. The calorimeter measures only how much heat, on average, was removed from the sample after a given time in the freezer.

Most of the enthalpy change occurred soon after the sample was placed in the freezer. Temperature measurements of the sample showed that sample regions near the surface reached the freezing point within 5 to 10 minutes. For all samples, the heat removed rose steadily with time before reaching a steady state value. The time required to reach a steady-state varied with the product, freezer temperature, air speed, and type of freezer. In general, faster freezing was achieved with cryogenic freezing, lower temperature, higher air speed, and 3-dimensional versus 1-dimensional freezing.

5. Temperature Profiles

For most samples, initial cooling to the freezing point was fairly rapid; this is most likely due to the fact that less heat must be removed to cool liquid water than to induce a phase change to ice. After 15–20 mins, the freezing temperature is approached (about −1° C.), and temperatures throughout the sample began to diverge. As expected, temperatures at points closest to the surface decrease most rapidly.

After the freezing point was reached, temperatures tended to plateau before lowering further. This was more prominent at points farthest from the surface. This is indicative of a system undergoing a first order phase transition. The process is isothermal as heat is removed to change water into ice. As ice is formed in exterior regions, the thermal gradients for moving heat away from interior regions is reduced; thus, it takes longer to form a given volume of ice as freezing progresses. After approximately 120 mins, all temperatures converge. This corresponds to a low value of signal intensity in the NMR images.

Locations of the trailing end of the interface (as a function of the time spent in the freezer) were determined for beef roundsteak from the NMR images by measuring the distance between the bright areas and the edge of the slabs. Temperature profiles recorded with the thermocouples at three different locations along the freezing slabs indicated that the phase change occurs over a temperature range rather than at constant temperature.

6. Freezing Model Analysis

As a test of the enthalpy based freezing model, analysis was done for one-dimensional freezing of beef or ground beef (dimensions=3 cm×3 cm×4.5 cm). As previously mentioned, the advance of the ice front was not symmetrical between front and rear surfaces. The asymmetrical, one-dimensional heat transfer phenomena were simplified by assuming that each slab consisted of two imaginary half-slabs joined together at the latest freezing line. Heat transfer was simulated separately for each half-slab using the mathematical model of Mannaperuma and Singh. Simulations of the temperature profiles along the beef and ground beef indicate that the simulations and the experimental data correspond with less than ±2° C. error. Convective heat transfer coefficients were found by trial and error procedure to obtain the minimum sum of squares error between the model and the experimentally measured temperatures. They were 140 and 100 W/m² °C. for beef, 130 and 80 W/m² °C. for ground beef half-slabs.

Values of the convective heat transfer coefficent, h, depend on the velocity and physical properties of the air stream as well as the shape of the product. Ilicali and Saglam reported values between 13.8 and 64.8 W/m² °C. for freezing Golden Delicious apples. Mannaperuma and Singh, studying freezing of tylose spheres, reported h=300 W/m² °C. De Reinick and Schwartzberg reported h=15 to 22 W/m² °C. for beef patties. Considering the dependence of h on various factors, it is clear that the values found in this study are of similar magnitude, but may be high estimates when compared with the other results for beef.

Enthalpy removed during freezing per cross sectional area of a slab were simulated for various times spent in the freezer. The mathematical model assumes that the phase change is initiated between −1° C. and −2° C. Our observations based on NMR images indicate that there is not a significant amount of ice formed until the temperature has reached −2° C. The phase change appears to be essentially completed by the time the temperature reaches −5° C. These observations are as expected and suggest that it may be possible to improve mathematical descriptions of the freezing interface by detailed analyses of the NMR images.

7. Spatial Resolution Required for NMR Sensors

The minimum spatial resolution for an NMR sensor can be estimated from the calculated error in the enthalpy per volume defined by the resolution distance times the cross-sectional area. The resolution distance determines how much volume of ice may be formed without being detected by the sensor, and thus defines the error in determining product enthalpy. The assumptions and definitions are as follows:

(a) The position of the ice interface will be defined as the region with the largest slope within the image.

(b) No signal from solid-like protons is recorded. This is reasonable as the solid-like signal decays 4–6 orders of magnitude faster than the liquid-like signal.

(c) One-dimensional freezing of a uniform object will be the test case. Freezing in 2 or 3 dimensions will have an inherently lower error.

(d) Spatial resolution required will depend upon the size of the object being frozen. Long, thin objects will require less resolution along the length than wide, short objects.

(e) As material near the interface will be close to the freezing temperature, only latent heat changes will be considered.

If, for example, it is required that the enthalpy estimation is within 2.5% of the actual value, we can write:

$$2.5\% = \frac{100 \, \delta H}{\Delta H_{tot}}$$

where $\Delta H_{tot}$=total enthalpy change=initial enthalpy—storage enthalpy $\delta H$=enthalpy error=$L_i \times w \times h \times \Delta H_f$ $\Delta H_f$=latent heat of fusion w=sample width h=sample height $L_i$=resolution in the frequency encoded direction $L = \Sigma L_i$=total sample width For a slab type geometry, the required resolution is $$L_i = \frac{0.025 \, H_{tot}}{wh\Delta H_f}$$

while for a cylindrical object $$L_i = \frac{0.025 \, H_{tot}}{\pi r^2 \Delta H_f}$$

As an example, consider a french fried potato 1×1×10 cm with 77% moisture and a density of 900 kg/m³. The heat of fusion is given by $$\Delta H_f = 0.77 \times 333.2 \text{ J/g} = 256.6 \text{ J/g}$$

From calorimetry experiments, the total enthalpy removed in cooling and freezing a potato from 25° C. to −30° C. is $\Delta H_{tot}$=350 J/g. Thus, the required spatial resolution to ensure a 2.5% error limit is $$L_i = \frac{0.025(350 \text{ J/g})}{(.01 \text{ m})(.01 \text{ m})(900 \text{kg/m}^3)(1000 \text{ g/kg})(256.6 \text{ J/g})} =$$

$$3.8 \times 10^{-4} = 380 \, \mu m$$

Similarly, for a 2.5 cm diam×3 cm cylindrical potato $$L_i = \frac{0.025(350 \text{ J/g})}{\pi(.0125 \text{ m})^2 (900 \text{kg/m}^3)(1000 \text{ g/kg})(256.6 \text{ J/g})} =$$

$$7.7 \times 10^{-5} = 77 \, \mu m$$

the present system maintained a spatial resolution of 340 μm. Resolutions on the order of 100 μm could readily be obtained. Alternatively, a greater error in the enthalpy measurement may be acceptable. The resolution requirements would then be reduced as $L_i \, \alpha \%Error$.

8. Temporal Resolution Required for NMR Sensors

Specific temporal constraints depend upon several features of the freezing operation/sensor system, especially product throughput rate and data acquisition times. These restraints define the length of field that must be highly homogeneous in order to ensure good imaging. To calculate temporal restraints, we made the following assumptions:

(a) Maximum conveyor belt speed is 1 m/sec.

(b) Time to acquire data is 100 msec.

(c) Approximately 100 msec is required to establish enough polarization of sample to record an adequate signal.

(d) 10% contingency.

The length of the magnetic field is given by $L_B$ = 1.1 × experimental time × product velocity = 1.1 × (100 msec + 100 msec) × 1 m/sec = .22 m ≈ 22 cm Only a small section of the magnet needs to have good homogeneity, that is, the region used for the NMRI measurement. For a small sample, about one-third of the field (8 cm) would be occupied by sample and require high homogeneity. Two-thirds (14 cm) could be a low homogeneity field. For larger samples, such as an 8 cm ear of corn, the length would be length of sample+(1.1×0.200 sec×1 m/sec)

The largest field would be on the order of 8+22=30 cm, with approximately 16 cm required to be highly homogeneous.

In practice, three field gradients are required with linearity of 5% over twice the sample size. A low field strength permanent magnet should be adequate.

9. Conclusion

Accordingly, it will be seen that this invention provides an apparatus and method for accurate in-line, non-invasive determination of enthalpy of a food product through the use of NMR or NMRI to determine the ice content. As freezing is an energy intensive process, it is important to move the food through the freezer at the fastest rate possible. Once the desired enthalpy change has been achieved, further time in the freezer wastes energy and limits throughput. Conversely, it is crucial that the product remain in the freezer as long as necessary. While frozen storage rooms are designed to prevent further heat gain or loss, they may not have the capacity to remove additional heat from a product that arrives underfrozen; if it does, this heat may not be removed in the most energy efficient manner. In addition, freezing in such a room is likely to be slower and result in lower product quality.

By locating the ice interface in a product using magnetic resonance imaging in accordance with the present invention, it can easily be determined when the desired enthalpy change has been achieved. The liquid state will be seen as areas of high signal intensity, whereas the frozen state will be seen as areas of low signal intensity. Therefore, the ice interface will be seen as the region where the NMRI signal changes most rapidly. Enthalpy changes can then be determined from this information based on conventional computer modeling of food freezing. For a given food product, the computer model is used to predict the spatial location of the ice interface in the product under specified freezing conditions (e.g., temperature) for various levels of enthalpy. The predicted location of the ice interface is then compared to the actual location derived from the NMRI signals. Using a differential calorimeter to measure the true enthalpy corresponding to the position of the ice interface seen from the NMRI signals, the computer model is then calibrated to match the actual position of the ice interface for that enthalpy. Thereafter, the position of the ice interface determined from the NMRI signals can be correlated to enthalpy using the computer model. Alternatively, instead of using a computer model to correlate the position of the ice interface as seen from the NMRI images with enthalpy, the product is imaged to determine the total liquid portion and the total solid portion. The ratio of liquid to solid portions is then compared to calorimetry data for that product and a calibration curve is developed from the test data. Using that calibration curve, enthalpy can be determined as a function of the percent of total product which is frozen as seen from the NMRI signals. Further, for objects of regular, or symmetrical geometric shape, the ratio of liquid to solid portions can be determined without using NMRI signals and, instead, integrating the amplitude of NMR signals (e.g., signals without using the gradient coils to determine spatial information). With any of the methods, once the calibration has been effected, enthalpy is determined automatically by control processor 26 based on the acquired NMRI or NMR signals.

It will be appreciated that the method of the present invention may vary as to the steps and their sequence and that the apparatus of the present invention may vary as to configuration and as to details of the parts without departing from the basic concepts as disclosed herein. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A nuclear magnetic resonance freezing sensor, comprising:
   (a) means for subjecting an object containing fluid to nuclear magnetic resonance imaging and acquiring images of said object;
   (b) means for identifying the ice content in said object while said fluid freezes from said images; and
   (c) means for determining a change in enthalpy of said object from the ice content.

2. An apparatus for monitoring freezing of foods, comprising:
   (a) means for subjecting an object containing water to nuclear magnetic resonance imaging and acquiring images of said object;
   (b) means for identifying the position of the ice interface in said object from said images as sufficient heat is removed from said object for said water to freeze; and
   (c) means for determining a change in enthalpy of said object from the position of the ice interface.

3. An apparatus for measuring changes in enthalpy during controlled freezing of food, comprising:
   (a) means for subjecting an object containing fluid to nuclear magnetic resonance imaging and acquiring images of said object;
   (b) means for determining the position of a transition for high to low signal intensity in said images as said fluid freezes; and
   (c) means for determining a change in enthalpy of said object from said intensity transition.

4. An apparatus for sensing the changes in enthalpy during transition from a liquid to solid state during controlling freezing of food, comprising:
   (a) means for subjecting an object containing fluid to nuclear magnetic resonance imaging;
   (b) means for acquiring images of liquid portions of said object from said nuclear magnetic resonance imaging;
   (c) means for acquiring images of solid portions of said object from said nuclear magnetic resonance imaging;
   (d) means for determining the liquid/solid ratio of said object from said images;
   (e) means for determining a change in enthalpy of said object from said liquid/solid ratio.

5. An apparatus for sensing the changes in enthalpy during transition from a liquid to solid state during controlling freezing of food, comprising:
   (a) means for subjecting an object containing fluid to nuclear magnetic resonance signals;
   (b) means for determining the liquid/solid ratio of said object from said signals during freezing of said object; and
   (c) means for determining a change in enthalpy of said object from said liquid/solid ratio.

6. A method of sensing freezing of an object, comprising:
   (a) subjecting an object containing fluid to nuclear magnetic resonance imaging and acquiring images of said object;
   (b) identifying the ice content in said object from said images while said fluid freezes; and
   (c) determining a change in enthalpy of said object from the ice content.

7. A method of sensing freezing of foods, comprising:
   (a) subjecting an object containing water to nuclear magnetic resonance imaging and acquiring images of said object;
   (b) identifying the position of the ice interface in said object from said images as sufficient heat is removed from said object for said water to freeze; and
   (c) determining a change in enthalpy of said object from the position of the ice interface.

8. A method of measuring changes in enthalpy during controlled freezing of food, comprising:
   (a) subjecting an object containing fluid to nuclear magnetic resonance imaging and acquiring images of said object;
   (b) determining the position of a transition for high to low signal intensity in said images as said fluid freezes; and
   (c) determining a change in enthalpy of said object from said intensity transition.

9. A method of sensing the changes in enthalpy during transition from a liquid to solid state during controlling freezing of food, comprising:
   (a) subjecting an object containing fluid to nuclear magnetic resonance imaging;
   (b) acquiring images of liquid portions of said object from said nuclear magnetic resonance imaging;
   (c) acquiring images of solid portions of said object from said nuclear magnetic resonance imaging;
   (d) determining the liquid/solid ratio of said object from said images during freezing of said object;
   (e) determining a change in enthalpy of said object from said liquid/solid ratio.

10. A method of sensing the changes in enthalpy during transition from a liquid to solid state during controlling freezing of food, comprising:
    (a) subjecting an object containing fluid to nuclear magnetic resonance signals;
    (b) determining the liquid/solid ratio of said object from said signals during freezing of said object; and
    (c) determining a change in enthalpy of said object from said liquid/solid ratio.

* * * * *